United States Patent [19]
Vedage et al.

[11] Patent Number: 5,917,092
[45] Date of Patent: Jun. 29, 1999

[54] METAL EXCHANGED ZEOLITE CATALYSTS FOR ALCOHOL AMINATION

[75] Inventors: Gamini Ananda Vedage, Bethlehem; Lenore Ann Emig, Whitehall; Hong-Xin Li, Allentown; John Nelson Armor, Orefield, all of Pa.

[73] Assignee: Air Products and Chemicals, Inc., Allentown, Pa.

[21] Appl. No.: 09/049,540

[22] Filed: Mar. 27, 1998

[51] Int. Cl.$^6$ .................................................. C07C 209/38
[52] U.S. Cl. ............................................................ 564/480
[58] Field of Search ............................................. 564/480

[56] References Cited

U.S. PATENT DOCUMENTS

| | | | |
|---|---|---|---|
| 3,384,667 | 5/1968 | Hamilton | 260/585 |
| 4,036,883 | 7/1977 | Voges et al. | 260/585 B |
| 4,082,805 | 4/1978 | Kaeding | 260/585 |
| 4,254,061 | 3/1981 | Weigert | 564/479 |
| 4,255,357 | 3/1981 | Gardner et al. | 564/480 |
| 4,398,041 | 8/1983 | Cochran et al. | 564/479 |
| 4,760,190 | 7/1988 | Twigg | 564/480 |
| 4,918,234 | 4/1990 | Deeba | 564/480 |
| 5,600,000 | 2/1997 | King | 564/480 |
| 5,808,158 | 9/1998 | Conrads et al. | 564/480 |

*Primary Examiner*—Brian M. Burn
*Attorney, Agent, or Firm*—Mary E. Bongiorno

[57] ABSTRACT

A process for the production of predominantly primary and secondary amines and little or no tertiary amines by the reductive amination of aliphatic alcohols using a metal exchanged crystalline aluminosilicate catalyst. The catalyst has a silica/alumina ratio ranging from about 10:1 to 40:1, contains about 1 to 10% by weight of cobalt or nickel and about 0.05 to 5% by weight of at least one other metal. High conversion rates are achieved at moderate temperatures and pressures.

8 Claims, 1 Drawing Sheet

METAL EXCHANGED ZEOLITE CATALYSTS FOR ALCOHOL AMINATION

BACKGROUND OF THE INVENTION

The catalyzed reaction of alkanols with ammonia or amines to produce a mixture of alkylamines is known. Various catalysts are also known for use in the amination process. For example, cobalt, nickel, copper, and palladium, have been used in the reductive amination of alcohols; and, silica-alumina and zeolite-type catalysts have been used in the direct amination of alcohols.

Production of a non-equilibrium distribution of products from the amination process is often desired and has been achieved by altering reaction conditions and/or catalyst systems. Examples of catalyst systems used to produce a non-equilibrium split of alkyl amines are described below:

U.S. Pat. No. 3,384,667 (Hamilton, 1968) discloses a method of producing primary and secondary amines in preference to tertiary amines by reacting an alcohol with ammonia in the presence of a dehydrated crystalline metal aluminosilicate catalyst having a pore size of 5 to about 10 Å. The original metal in the aluminosilicate catalyst can be replaced by a variety of cations, such as barium, calcium, and magnesium. Appropriate reaction temperatures were reported to be 200 to 300° C.

U.S. Pat. No. 4,082,805 (Kaeding, 1978) discloses a process for producing primary aliphatic amines over secondary or tertiary amines by reacting a $C_1$–$C_5$ alcohol or ether with ammonia in the presence of an aluminosilicate catalyst having a high silica to alumina ratio; i.e., greater than 5 and preferably greater than 30. Operative catalysts include ZSM-5, ZSM-11 or ZSM-21. Reaction temperatures are 300 to 500° C.

U.S. Pat. No. 4,254,061 (Weigert, 1981) discloses a catalytic process for making monomethylamine in which methanol and ammonia, in amounts so as to provide a carbon/nitrogen ratio of 0.5 to 1.5, are reacted over a dehydrated crystalline aluminosilicate catalyst selected from:

mordenite wherein the primary cation is Li, Na, K. Ca, Sr, Ba, Ce, Zn, or Cr;

ferrierite wherein the primary metal cation is Li, Na, K. Ca, Sr, Ba, Ce, or Fe;

erionite ore;

calcium erionite; and clinoptilolite ore.

The reaction temperature is 250 to 475° C. at pressures of 1–1000 psi.

U.S. Pat. No. 4,398,041 (Cochran et al., 1983) discloses a two-stage process for converting $C_1$–$C_4$ alcohol to a non-equilibrium controlled distribution of primary, secondary, and tertiary amines. Shape selective crystalline aluminosilicate zeolite catalysts are used in the process which is conducted at temperatures between about 250 to 425° C.

U.S. Pat. No. 4,918,234 (Deeba, 1990) discloses an improved process for producing $C_2$ to $C_4$ alkylamines by the reaction of a $C_2$ to $C_4$ alkanol with ammonia in the presence of hydrogen and a crystalline aluminosilicate catalyst at temperatures of 170 to 220° C., to produce non-equilibrium split of alkylamines. The crystalline aluminosilicate zeolite catalyst system is a Y zeolite containing predominantly cobalt or nickel ions.

BRIEF SUMMARY OF THE INVENTION

This invention is directed to an improved process for reductive amination of aliphatic alcohols to form predominantly primary and secondary amines using a metal exchanged crystalline aluminosilicate catalyst. A $C_1$ to $C_{10}$ aliphatic alcohol is reacted with ammonia in the presence of hydrogen and a catalyst having a silica/alumina ratio ranging from about 10:1 to 40:1 and containing cobalt or nickel together with at least one other metal. Specifically, the catalyst contains about 1 to 10% by weight cobalt or nickel and about 0.05 to 5% by weight of at least one other metal selected from an alkali metal, an alkaline earth metal or a rare earth metal.

Some of the advantages of using the catalyst of this invention include:

Predominantly primary and secondary amines and little or no tertiary amines can be produced at moderate temperatures and pressures;

Predominantly primary amines can be produced with branched alcohols such as isopropanol;

High conversion rates are achieved with a relatively small amount of cobalt or nickel in the catalyst; and There is little or no deactivation of catalyst over several reaction runs.

DETAILED DESCRIPTION OF THE INVENTION

Figure 1:
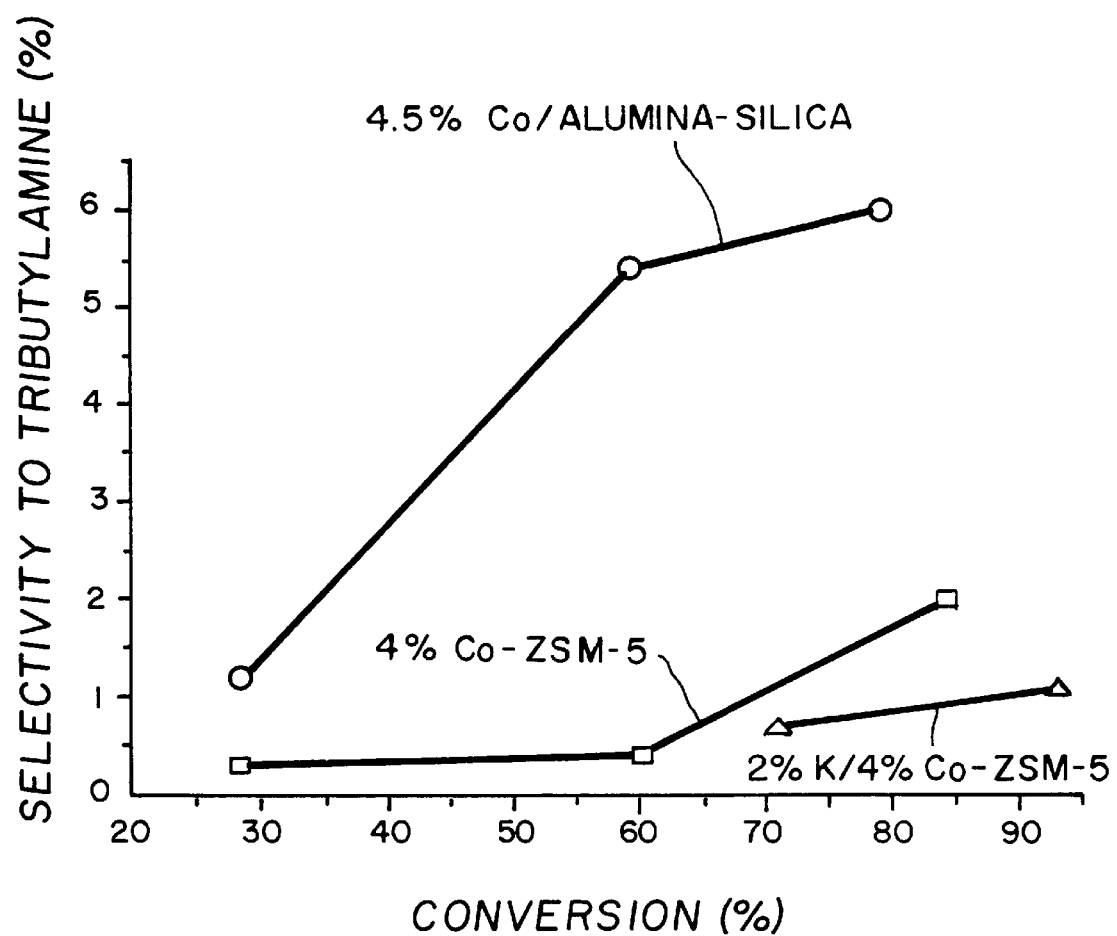
FIG. 1 shows selectivity to tertiary amines as a function of conversion in the amination of butanol, for three catalysts: 4.5% cobalt/silica alumina; 4% cobalt-ZSM-5 zeolite; and 2% potassium/4% cobalt-ZSM-5 zeolite.

The catalyst of this invention is particularly useful in the production of predominantly primary and secondary aliphatic amines by the reaction of an aliphatic alkanol with ammonia. The catalyst is a cobalt or nickel-exchanged crystalline aluminosilicate zeolite catalyst having a silica to alumina ratio of about 10:1 to 40:1, preferably 20:1 to 30:1, in which the cations which has been doped with at least one other metal.

Examples of appropriate aluminosilicate zeolites are: ZSM-5, ZSM-11, and ferrierite. ZSM-5 type zeolite is preferred. The cations in the crystalline aluminosilicates may be readily exchanged with other cations by any of known methods; for example, ion exchange treatment. The crystalline aluminosilicate zeolite of this invention is converted to a form in which up to about 10% by weight of cations are cobalt or nickel. The cobalt or nickel-exchanged zeolite is then doped, i.e., further exchanged, with one or more other metal, such as an alkali metal, alkaline earth metal or a rare earth metal. By rare earth metals is meant group IIIB metals (lanthanide series) or metals having an atomic number of 57 to 71. Examples of appropriate metals are lithium, sodium, potassium, magnesium, calcium, strontium, cerium, and lanthanum. Preferred metals are potassium, sodium, and magnesium. The resulting zeolite catalyst contains 1 to 10% by weight, preferably 2 to 5% by weight, cobalt or nickel, and 0.5 to 5% by weight, preferably 1 to 3% by weight, of one or more other metal.

The alcohol reactant can be a $C_1$ to $C_{10}$ aliphatic alcohol; especially a $C_2$ to $C_4$ alcohol. Examples of appropriate alcohols include methanol, ethanol, propanol, isopropanol, butanol, isobutanol, tert-butyl alcohol, pentanol, hexanol, and cyclohexanol.

Production of aliphatic amines in the presence of metal-containing aluminosilicate catalyst and hydrogen is effected by contact of ammonia with alcohol at a temperature between about 150 and 250° C.; preferably 190 and 225° C. Reaction pressure can range from about 1 to 50 atmospheres; usually 10 to 30 atmospheres. The relative feed rates, expressed as moles, of ammonia (N) to alcohol (R) are generally within the range of about 1:1 to 20:1; preferably from 2:1 to 10:1. The relative feed rates of hydrogen (H) to alcohol (R), expressed as moles, are generally 0.5:1 to 20:1; preferably 1:1 to 5:1. Flow rates (GHSV) range from about 500 to 30,000 cc of reactants per cc of catalyst per hour, preferably 1000 to 2000 $hr^{-1}$.

It was found, unexpectedly, that doping the zeolite catalyst with a metal, other than cobalt or nickel, resulted in a superior catalyst for the reductive amination of lower aliphatic alcohols to produce a slate of predominantly primary and secondary amines. A relatively small amount of the other metal, such as potassium or magnesium, resulted in a stable catalyst with enhanced activity.

The invention will be further clarified by a consideration of the following examples, which are intended to be purely exemplary of the invention.

EXAMPLES

Catalysts were prepared according to the following general procedures:

4 wt. % Cobalt Exchange

Cobalt acetate tetrahydrate (47 g) was dissolved in 3.8 liters of deionized (DI) water. After the cobalt salt was completely dissolved, 229 g of $NH_4$-ZSM-5 (SM27, supplied by VAW Aluminium AG) was added to the cobalt salt solution. Initial pH was 6.9. The solution was heated to 80° C. and stirred approximately 20 hours. Final pH was 5.2. The solution was cooled to 60° C., and the Co-ZSM-5 was filtered and rinsed with DI water. The above procedure was repeated two more times. After the third exchange, the catalyst was filtered, suspended in 2.9 liters of DI water, and stirred for 1 hour. It was then dried overnight under nitrogen at 110° C.. The final material contained about 4 wt. % cobalt.

Doping with Potassium, Sodium, Magnesium, Calcium and Cerium

In general, a metal salt was dissolved completely in 4–5 ml deionized (DI) water. The cobalt exchanged zeolite was added to the metal salt solution quickly with stirring. Catalyst was just wet. More DI water was added drop-wise, if needed, to facilitate mixing. The metal-doped Co-ZSM-5 catalysts were then dried at 110° C. to yield the final catalyst.

Potassium Doping

A 2% K/Co-ZSM-5 was prepared by dissolving 0.75 g potassium acetate (or potassium nitrate) in DI water, and adding 15 g Co-ZSM-5 and stirring well. The exchanged zeolite was dried and then calcined at 220° C. or 400° C. for 3 hours in air (2° C./min ramp).

Sodium Doping

A 2.8 %Na/Co-ZSM-5 catalyst was prepared by dissolving 1.99 g sodium acetate (or sodium nitrate) in DI water, adding 11.7 g Co-ZSM-5, and stirring well. The catalyst was dried and then calcined at 500° C. for 3 hours in air (2° C./min ramp).

Magnesium Doping

A 1.2%Mg/Co-ZSM-5 catalyst was prepared by dissolving 1.96 g magnesium acetate hexahydrate in DI water, adding 15 g Co-ZSM-5, and stirring well. The catalyst was then dried and then calcined at 200° C. or 400° C. for 3 hours.

Calcium Doping

A 1.8%Ca/Co-ZSM-5 catalyst was prepared by dissolving 1.21 g calcium acetate hydrate in DI $H_2O$ and adding 15 g Co-ZSM-5. After stirring well it was dried and then calcined at 400° C.

Cerium Doping

A 1.6%Ce/Co-ZSM-5 was prepared by dissolving 0.93 g cerium nitrate hexahydrate in DI water, adding 15 g Co-ZSM-5, and stirring well. It was dried and then calcined at 500° C. for 3 hours in air (2° C./min ramp).

Catalyst Testing

Experiments were conducted in a continuous flow, packed bed reactor. The reactor had two liquid and two gas feed lines. The liquid feed lines were used to deliver ammonia and alcohol while the gas feed lines were used to deliver hydrogen and nitrogen. The plug flow reactor was a ½ inch internal diameter, 1 foot long tube. The catalyst was placed in the middle of the reactor. The top of the reactor was filled with quartz wool and the bottom of the reactor was filled with quartz chips and wool.

All catalysts were activated at either 400 or 500° C. Hydrogen/nitrogen mix (14.3 liters/hr hydrogen/8.0 liters/hr nitrogen) was used to reduce the catalyst for 2 hours at temperature using a 2° C./min ramp. After reduction of the catalyst, the temperature was decreased to amination reaction temperature.

Example 1

Potassium Doped Cobalt Catalysts for Amination of Butanol

Three catalysts (4% Co-ZSM-5, 2% K/4% Co-ZSM-5 and 4.5% Co/silica-alumina) were tested. The results are shown in Table 1. The potassium acetate (KOAc) or potassium nitrate (KNO3) doped Co-ZSM-5 zeolites will be referred to as 2% K/4% Co-ZSM-5. As shown in Table 1, the 4% Co-ZSM-5 and 4.5% Co/silica-alumina had similar activity at 206° C. to 225° C.; however, there was a difference in their level of tributylamine selectivity. Surprisingly, at lower temperatures (190° C.), 2% K/4% Co-ZSM-5, was about twice as active as 4% Co-ZSM-5 or 4.5% Co/silica-alumina. Without being bound by theory, the higher activity of the 2% K/4% Co-ZSM-5 catalyst might be attributed to a higher surface area. The 2% K/4% Co-ZSM-5 catalyst had a metal surface area of 2.5 $m^2$/g while the 4% Co-ZSM-5 catalyst had a surface area of 0.6 $m^2$/g.

Another major difference between 2% K/4% Co-ZSM-5 and amorphous 4.5% Co/silica-alumina catalysts was in the selectivity to tertiary amines. FIGURE 1 is a plot of tertiary amine selectivity as a function of conversion, for the three catalysts. As the conversion increases, typically the tertiary amines also increase. Increasing the conversion of 4.5%Co/silica-alumina catalyst from 30% to 80%, increased tertiary amine selectivity from 1.2% to 6.0%. Using 4% Co-ZSM-5 catalyst and increasing conversion from 30% to 60% did not increase tertiary amines significantly. In order to obtain 60 to 85% conversion using 4% Co-ZSM-5 catalyst, the temperature was raised from 207° C. to 225° C. which also raised the production of tertiary amines from 0.4% to 2.0%. In contrast, increasing the temperature from 192 to 212° C., increased conversion with 2% K/4% Co-ZSM-5 catalyst from 70% to 93%. However, there was only a marginal increase in tertiary amines (1.1% at 212° C. compared to 0.7% at 192° C.). A substantially constant product slate shown by the 2% K/4% Co-ZSM-5 catalyst at two different temperatures indicates that the selectivity of the catalyst is at least partly due to the shape selectivity of the catalyst.

In addition to maintaining selectivity to primary and secondary amines, the 2% K/4% Co-ZSM-5 was stable during a week of testing. In order to determine reproducibility, the reaction was cycled back and forth between 190° C. and 210° C. Conversions and selectivity were reproducible, indicating that the potassium doped Co-ZSM-5 catalyst was very stable under the conditions used. In comparison, the 4% Co-ZSM-5 was not stable; in fact, it became inactive after 48 hours.

TABLE 1

| Catalyst | Time on Stream (hrs) | Temp (° C.) | Pressure (psi) | Conversion (%) | Selectivity | | |
|---|---|---|---|---|---|---|---|
| | | | | | BuNH$_2$ | Bu$_2$NH | Bu$_3$N |
| 4% Co-ZSM-5 | 22 | 207 | 324 | 60.0 | 63.6 | 35.7 | 0.4 |
| | 28.5 | 225 | 322 | 84.4 | 54.9 | 42.8 | 2.0 |
| 4.5% Co/silica-alumina | 24 | 206 | 338 | 59.3 | 69.9 | 33.7 | 5.4 |
| | 48 | 222 | 341 | 79.2 | 50.0 | 43.8 | 6.0 |
| 2% K/4% Co-ZSM-5 | 6.8 | 214 | 347 | 94.3 | 53.5 | 45.6 | 0.6 |
| | 13.5 | 190 | 359 | 72.3 | 63.5 | 34.7 | 1.2 |
| | 29.0 | 212 | 333 | 93.0 | 51.2 | 47.5 | 1.1 |
| | 50.6 | 192 | 365 | 70.8 | 64.4 | 34.8 | 0.7 |

GHSV = 1100/hr; N/R/H = 5.4/1/5.3

Example 2

Other Catalysts for Amination of Butanol

Several catalysts were prepared in which the amount of cobalt and potassium in different zeolites was varied. The general procedure as set forth for the ZSM-5 catalysts was used in preparation of these catalysts. Data was collected on the performance of each catalyst in the amination of butanol. They are presented in Table 2 below.

TABLE 2

| Catalyst | Temp. (° C.) | Pressure (psi) | Conversion (%) | Selectivity | | |
|---|---|---|---|---|---|---|
| | | | | BuNH$_2$ | Bu$_2$NH | Bu$_3$N |
| 6% Na/14% Co-Linde A | 210* | 380 | 84.6 | 64.2 | 32.7 | 3.1 |
| | 190 | 370 | 27.4 | 83.4 | 16.0 | 0.6 |
| 2% K/6% Co-Ferrierite | 210 | 381 | 66.7 | 60.2 | 37.4 | 2.3 |
| | 225 | 380 | 82.0 | 51.5 | 45.7 | 2.9 |
| 2% K/2.3% Co-beta Zeolite | 211 | 362 | 44.8 | 69.2 | 27.2 | 2.9 |
| | 225 | 279 | 68.2 | 41.9 | 49.1 | 8.3 |
| | 240 | 311 | 87.0 | 36.4 | 52.8 | 10.4 |
| 2% K/7% Co-Mordenite | 210 | 310 | 92.9 | 42.1 | 51.3 | 6.2 |
| | 190 | 355 | 70.9 | 56.3 | 39.8 | 4.0 |
| 2% K/10% Co-Y-Zeolite | 210 | 370 | 93.0 | 35.6 | 57.6 | 4.5 |
| | 190 | 380 | 78.9 | 75.1 | 23.3 | 0.9 |
| 2% K/15% Co-Na$^+$ Chabazite** | 210 | 370 | 93.8 | 41.3 | 48.4 | 9.9 |
| | 190 | 370 | 80.3 | 42.8 | 47.1 | 9.7 |
| HZSM-5 | 210 | 370 | 0 | | | |

GHSV = 1100/hr  N/R/H = 5.4/1/5.3
*GHSV = 1395/hr  N/R/H = 5.5/1/10.42
**X-ray diffraction studies showed that the structure of chabazite collapsed after cobalt exchange.

Comparing the data presented in Tables 1 and 2, the activity of the catalysts decreased in the following order: 2% K/4% Co-ZSM-5≅2%K/15% Co-Chabazite≅2% K/10% Co-Y Zeolite≅2% K/7% Co-Mordenite>2% K/14%Co-Linde A>2% K/6% Co-Ferrierite>4% Co-ZSM-5≅4.5%Co/SiO$_2$Al$_2$O$_3$>2% K/2.3% Co-beta Zeolite.

The selectivity to primary and secondary amines of the above catalysts decreased in the following order: 2% K/4% Co-ZSM-5>4% Co-ZSM-5>2% K/14%Co-Linde Linde A≅2% K/6% Co-Ferrierite>2% K/10% Co-Y Zeolite>2% K/7% Co-Mordenite>2%K/15% Co-Chabazite≅4.5%Co/SiO$_2$Al$_2$O$_3$>2% K/2.3% Co-beta Zeolite.

Based on these data, the 2% K/4% Co-ZSM-5 catalyst had the highest activity as well as the best selectivity for the amination of butanol to mono- and di-butylamines.

Example 3

Effect of Si/Al Ration of ZSM-5 on Butanol Amination

Table 4 contains the results of experiments to study the effect of Si/Al ratio on the activity and selectivity of K/Co-ZSM-5 in butanol amination. The results show that as the Si/Al ratio increased, the level of exchangeable cobalt decreased. At a Si/Al ratio of 12:1, the level of exchangeable cobalt is about 4%, at 20:1 it is about 2% and at 90:1 the level of exchangeable cobalt drops to about 0.5%. Since the activity of these catalysts is due to cobalt, as the level of cobalt decreased the activity also decreased. Hence, the highest activity was seen with 2% K/4% Co-ZSM-5 (Si/Al= 12:1) and the lowest activity was seen with 2% K/0.5% Co-ZSM-5 (Si/Al=90:1).

No more than about 0.5% cobalt was achieved with ion exchange in a K/Co-ZSM-5catalyst having a Si/Al of 90. In order to increase conversion using this catalyst, the temperature was increased to 250° C. and the feed flow rate was lowered by half.

TABLE 3

| Catalyst | Si/Al | Temperature ° C. | % Conversion | % Selectivity | | |
|---|---|---|---|---|---|---|
| | | | | BuNH$_2$ | Bu$_2$NH | Bu$_3$N |
| 2% K/4% Co-ZSM-5 | 12 | 210 | 93 | 51.2 | 47.5 | 1.1 |
| | | 190 | 70.8 | 64.4 | 34.8 | 0.7 |
| 2% K/2% Co-ZSM-5 | 20 | 210 | 73.4 | 67.1 | 31.6 | 1.0 |
| | | 225 | 85.3 | 60.8 | 37.4 | 1.4 |
| 2% K/0.5 Co-ZSM-5 | 90 | 210 | 16.2 | 97.2 | 2.1 | 0.0 |
| | | 250* | 48 | 90 | 10 | 0 |

GHSV = 1100 hr$^1$  N/R/H = 5.4/1/5.3
*N/R = 2

Example 4

Effect of Doping Cobalt-ZSM-5 Zeolite Catalysts with Different Cations

Table 5 presents data on the results of testing 4% Co-ZSM-5 catalysts that have been doped with several different cations.

TABLE 4

| CATALYST | Temp (° C.) | Pressure (psi) | Conversion (%) | % Selectivity BuNH$_2$ | % Selectivity Bu$_2$NH | % Selectivity Bu$_3$N | MSA* m$^2$/g | Comments |
|---|---|---|---|---|---|---|---|---|
| 2% K/4% Co-ZSM-5 | 210 | 358 | 93.0 | 51.2 | 47.5 | 1.1 | 2.0 | |
| | 190 | 359 | 72.3 | 63.5 | 34.7 | 1.2 | | |
| 2% Mg/4% Co-ZSM-5 | 210 | 342 | 86.8 | 72.4 | 27.6 | 0.0 | 2.5 | |
| 1.2% Mg/4% Co-ZSM-5 | 210 | 342 | 85.3 | 73.6 | 26.0 | 0.0 | | t = 4 hrs |
| | 210 | 342 | 86.8 | 72.4 | 27.3 | 0.0 | | t = 8 hrs |
| 2.8% N/4% CO-ZSM-5 | 212 | 350 | 91.4 | 63.2 | 33.2 | 3.2 | | t = 24 hrs |
| 2% Ca/4% Co-ZSM-5 | 212 | 333 | 51.9 | 71.7 | 26.4 | 1.6 | 4.5 | |
| 2% Ce/4% Co-ZSM-5 | 214 | 357 | 41.5 | 83.3 | 15.5 | 1.1 | 4.7 | t = 3 hrs |
| | 213 | 358 | 27.6 | 86.6 | 12.4 | 0.7 | | t = 8 hrs |

GHSV = 1100 hr$^{-1}$   N/R/H = 5.4/1/5.3
*MSA = metal surface area

Catalysts doped with either of potassium, magnesium, sodium, calcium, or cerium, showed good selectivity to primary and secondary amines. The best activity was achieved with catalysts doped with potassium, magnesium or sodium.

Example 5

Effect of Calcination Temperature

Table 6 presents data on the effect of calcination temperature on 4% Co-ZSM-5 catalysts doped with potassium and magnesium.

Potassium Doping

Testing was done using uncalcined potassium nitrate doped Co-ZSM-5 (4% K/4% Co-ZSM-5) samples, as well as samples calcined at 220° C. or 400° C. The activity of 220° C. and 400° C. calcined catalysts were very high compared to the uncalcined catalyst. However, the 220° C. calcined catalyst showed the highest selectivity; i.e., about 1% selectivity to tertiary amines.

Magnesium Doping

Magnesium nitrate doped Co-ZSM-5 (2.4% Mg/2% Co-ZSM-5) was calcined at 220° C. and 400° C. As shown in Table 6, the activity and the selectivity of this catalyst improved somewhat with calcination at 400° C.

TABLE 5

| Catalyst and Calcining Temp | Time on Stream (hrs.) | Temp (° C.) | % Conversion | % Selectivity BuNH$_2$ | % Selectivity Bu$_2$NH | % Selectivity Bu$_3$N |
|---|---|---|---|---|---|---|
| 4% K/4% Co-ZSM-5 220° C. | 8.3 | 212 | 97.67 | 47.68 | 51.37 | 0.95 |
| | 23.0 | 212 | 92.85 | 67.29 | 31.16 | 1.54 |
| 4% K/4% Co-ZSM-5 400° C. | 8.3 | 212 | 99.23 | 42.26 | 50.29 | 7.45 |
| | 23.9 | 212 | 98.39 | 54.32 | 40.40 | 5.29 |
| 4% K/4% Co-ZSM-5; not calcined | 15 | 212 | 90.46 | 67.08 | 30.43 | 2.04 |
| | 22.5 | 212 | 77.27 | 64.83 | 33.13 | 1.91 |
| 2.4% Mg/4% Co-ZSM-5 220° C. | 9.3 | 212 | 91.06 | 50.07 | 49.08 | 0.79 |
| | 57.8 | 212 | 95.71 | 53.19 | 43.17 | 3.64 |
| 2.4% Mg/4% Co-ZSM-5 400° C. | 8.2 | 212 | 98.94 | 51.07 | 47.88 | 1.05 |
| | 29.5 | 212 | 98.31 | 54.99 | 44.81 | 0.20 |

GHSV = 1065 hr$^{-1}$   N/R/H = 5.4/1/5.2

Example 6

Effect of Adding Magnesium or Cerium to Potassium Doped Co-ZSM-5 Catalysts

Two catalysts, one with 0.5%Ce/2% K/4% Co-ZSM-5 and one with 0.5%Mg/2% K/4% Co-ZSM-5 (Si/Al=12) were tested. As shown in Table 7, neither cerium nor magnesium had a beneficial effect on the catalytic activity of 2%K/4% Co-ZSM-5 catalyst. However, selectivity to primary and secondary amines remained high.

TABLE 6

| Catalyst | Temp (° C.) | Pressure (psi) | % Conversion | % Selectivity BuNH$_2$ | % Selectivity Bu$_2$NH | % Selectivity Bu$_3$N | Time on stream |
|---|---|---|---|---|---|---|---|
| 0.5% Ce/2% K/4% Co-ZSM-5 | 212 | 362 | 70.3 | 60.9 | 37.1 | 1.9 | 24 hrs |
| | 240 | 366 | 69.9 | 53.8 | 44.4 | 1.7 | 24 hrs |
| 0.5% Mg/2% K/4% Co-ZSM-5 | 213 | 370 | 41.3 | 77.0 | 15.2 | 7.5 | 8 hrs |
| | 240 | 375 | 64.07 | 62.5 | 35.2 | 2.1 | 8 hrs |

GHSV = 1100 hr$^{-1}$   N/R/H = 5.4/1/5.2

Example 7

Amination of Isopropanol with Ammonia over Co-ZSM-5 Catalysts

Table 8 shows the results of an isopropanol amination reaction using commercial 38% Co/Al2O3 (supplied by United Catalysts, Inc.) and 4%K/4% Co-ZSM-5 catalysts. These results show that a 4%K/4% Co-ZSM-5 catalyst gave excellent conversion to primary amines and high conversion was achievable with significantly less cobalt than in the commercial catalyst.

TABLE 7

| Catalyst | Time on stream, hr. | Temp °C. | % Conversion | % Selectivity | | |
|---|---|---|---|---|---|---|
| | | | | MIPA | DIPA | Unknowns |
| 4% K/4% Co-ZSM-5 | 8.5 | 212 | 100 | 96.7 | 2.8 | 0.0 |
| | 25.2 | 212 | 100 | 96.7 | 3.3 | 0.0 |
| 38% Co/alumina | 16.5 | 212 | 74.52 | 79.5 | 19.9 | 0.7 |
| | 25.8 | 212 | 100 | 81.0 | 18.6 | 0.5 |

GHSV = 1000 hr$^{-1}$   N/R/H = 5.3/1/5.3   250 psi

Example 8

Potassium Doped Nickel-ZSM-5 for Amination of Butanol

Table 3 shows an initial attempt to synthesize and test potassium doped Ni-ZSM-5 catalyst. The method of preparation was similar to preparing potassium doped Co-ZSM-5 catalysts (described earlier). This catalyst showed low activity but there was good selectivity to primary and secondary amines.

TABLE 8

| Catalyst | Temperature °C. | % Conversion | % Selectivity | | |
|---|---|---|---|---|---|
| | | | BuNH$_2$ | Bu$_2$NH$_2$ | BU$_3$N |
| 2% K/2.9%Ni-ZSM-5 | 210 | 10.3 | 13.2 | 79.7 | 5.3 |

GHSV = 1100
N/R/H = 5.4/1/5.3

What is claimed is:

1. A process for the production of predominantly primary and secondary amines and little or no tertiary amines by the reductive amination of aliphatic alcohols comprising:

reacting a $C_1$ to $C_{10}$ aliphatic alcohol with ammonia in the presence of hydrogen and a metal exchanged crystalline aluminosilicate catalyst having a silica/alumina ratio ranging between 10:1 to 40:1, wherein the aluminosilicate catalyst comprises 1 to 10 wt % of cobalt or nickel and 0.05 to 5 wt % of an alkali metal, an alkaline earth metal, or a rare earth metal.

2. The process of claim 1 wherein the aluminosilicate catalyst has a silica/alumina ratio of 20:1 to 30:1 and comprises 1 to 10 wt. % cobalt or nickel and about 0.5 to 5 wt. % of an alkali metal, an alkaline earth metal, or a rare earth metal.

3. The process of claim 1 wherein in the aluminosilicate catalyst comprises a ZSM-5 zeolite comprising 1 to 10 wt. % cobalt or nickel and 0.5 to 5 wt. % potassium, sodium or magnesium.

4. The process of claim 3 wherein the ZSM-5 zeolite comprises 2 to 5 wt. % cobalt and 1 to 3 wt. % potassium, sodium, or magnesium.

5. The process of claim 1, wherein the aliphatic alcohol is a $C_2$ to $C_4$ aliphatic alcohol.

6. The process of claim 1, wherein the aliphatic alcohol is isopropanol or n-butanol.

7. The process of claim 1, wherein the reaction is carried out at temperatures of about 190° C. and 225° C. and pressures of 10 to 30 atmospheres.

8. The process of claim 1, wherein the ammonia to alcohol ratio, expressed as moles, is from 2:1 to 10:1 and the hydrogen to alcohol ratio is from 1:1 to 5:1.

* * * * *